(12) United States Patent
Perreault et al.

(10) Patent No.: US 7,820,937 B2
(45) Date of Patent: Oct. 26, 2010

(54) METHOD OF APPLYING ONE OR MORE ELECTROMAGNETIC BEAMS TO FORM A FUSION BOND ON A WORKPIECE SUCH AS A MEDICAL DEVICE

(75) Inventors: Daniel Perreault, Bellevue, WA (US); Kristi Flury, Maple Grove, MN (US); Roger McGowan, Oakdale, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 103 days.

(21) Appl. No.: 10/974,300

(22) Filed: Oct. 27, 2004

(65) Prior Publication Data

US 2006/0086701 A1    Apr. 27, 2006

(51) Int. Cl.
*B23K 26/24* (2006.01)
*B29C 65/16* (2006.01)
*A61M 25/16* (2006.01)

(52) U.S. Cl. .............................. 219/121.64; 219/121.76

(58) Field of Classification Search ............ 219/121.61, 219/121.63, 121.64, 121.73, 121.76
See application file for complete search history.

(56) References Cited

U.S. PATENT DOCUMENTS

| | | | | |
|---|---|---|---|---|
| 3,774,010 A | * | 11/1973 | Heer et al. ............. | 219/121.85 |
| 3,821,510 A | * | 6/1974 | Muncheryan ........... | 219/121.79 |
| 3,984,153 A | * | 10/1976 | Zanoni ....................... | 359/487 |
| 4,289,378 A | * | 9/1981 | Remy et al. ................. | 359/368 |
| 4,488,277 A | * | 12/1984 | McFarlane et al. ........ | 369/47.28 |
| 4,549,288 A | * | 10/1985 | Chan ........................ | 369/47.35 |
| 4,598,039 A | * | 7/1986 | Fischer et al. ............... | 430/323 |
| 4,636,611 A | * | 1/1987 | Penney ................... | 219/124.34 |
| 4,714,815 A | * | 12/1987 | Swarts et al. ............ | 219/121.63 |
| 4,758,848 A | * | 7/1988 | Nakano ...................... | 347/236 |
| 4,794,231 A | * | 12/1988 | Banas et al. ............ | 219/121.63 |
| 4,818,049 A | * | 4/1989 | Assenheim et al. ........... | 385/35 |
| 4,859,827 A | * | 8/1989 | Coyle et al. ............. | 219/121.64 |
| 5,001,323 A | * | 3/1991 | Matsutani et al. ....... | 219/121.63 |
| 5,127,019 A | * | 6/1992 | Epstein et al. .............. | 372/108 |
| 5,267,959 A | * | 12/1993 | Forman ...................... | 604/103 |
| 5,339,380 A | | 8/1994 | Wysocki et al. ............. | 385/136 |
| 5,402,436 A | * | 3/1995 | Paoli ........................ | 372/50.12 |
| 5,412,678 A | * | 5/1995 | Treat et al. ................ | 372/45.01 |
| 5,501,759 A | * | 3/1996 | Forman ................... | 156/272.8 |
| 5,571,575 A | * | 11/1996 | Takayanagi .................... | 427/9 |

(Continued)

FOREIGN PATENT DOCUMENTS

DE    19527070 C1 * 10/1996

(Continued)

*Primary Examiner*—Samuel M Heinrich
(74) *Attorney, Agent, or Firm*—Crompton, Seager & Tufte, LLC (57) ABSTRACT

A process and apparatus is provided for forming a fusion bond between two materials. The process begins by forming a bond site by positioning a portion of a first body with respect to a portion of a second body. The first and second bodies may be components of a medical device such as a catheter, for example. At least one collimated beam of electromagnetic energy is generated and directed onto portions of the first and second bodies within the bond site so that at least one fusion zone having an increased temperature is formed.

32 Claims, 5 Drawing Sheets

U.S. PATENT DOCUMENTS

| | | | |
|---|---|---|---|
| 5,585,921 A * | 12/1996 | Pepper et al. | 356/487 |
| 5,645,739 A * | 7/1997 | Nakata et al. | 219/121.64 |
| 5,700,989 A * | 12/1997 | Dykhno et al. | 219/121.45 |
| 5,756,965 A * | 5/1998 | Mannava | 219/121.85 |
| 5,808,271 A * | 9/1998 | Duthoo | 219/121.64 |
| 5,841,098 A * | 11/1998 | Gedrat et al. | 219/121.63 |
| 5,874,708 A * | 2/1999 | Kinsman et al. | 219/121.64 |
| 5,957,930 A | 9/1999 | Vrba | |
| 5,958,268 A * | 9/1999 | Engelsberg et al. | 219/121.84 |
| 6,002,706 A * | 12/1999 | Staver et al. | 372/108 |
| 6,031,201 A * | 2/2000 | Amako et al. | 219/121.68 |
| 6,064,034 A * | 5/2000 | Rieck | 219/121.85 |
| 6,068,634 A | 5/2000 | Lorentzen Cornelius et al. | |
| 6,111,902 A * | 8/2000 | Kozlov et al. | 372/39 |
| 6,165,583 A * | 12/2000 | Boszormenyi | 428/848.3 |
| 6,201,211 B1 * | 3/2001 | Emmelmann | 219/121.63 |
| 6,242,063 B1 | 6/2001 | Ferrera et al. | |
| 6,331,186 B1 | 12/2001 | Wang et al. | |
| 6,391,528 B1 * | 5/2002 | Moshrefzadeh et al. | 430/321 |
| 6,462,307 B1 * | 10/2002 | Hennig et al. | 219/121.77 |
| 6,465,757 B1 * | 10/2002 | Chen | 219/121.63 |
| 6,478,814 B2 | 11/2002 | Wang et al. | |
| 6,545,246 B2 * | 4/2003 | Kummle | 219/121.63 |
| 6,563,082 B2 * | 5/2003 | Terada et al. | 219/121.72 |
| 6,570,125 B2 * | 5/2003 | Suh et al. | 219/121.76 |
| 6,608,280 B2 * | 8/2003 | Chen et al. | 219/121.76 |
| 6,657,160 B2 * | 12/2003 | Hackel et al. | 219/121.85 |
| 6,821,472 B2 * | 11/2004 | Schreiner et al. | 264/400 |
| 7,115,053 B2 * | 10/2006 | Meichner | 473/477 |
| 2002/0050488 A1 * | 5/2002 | Nikitin et al. | 219/121.64 |
| 2003/0193117 A1 * | 10/2003 | Schreiner et al. | 264/400 |
| 2003/0213787 A1 * | 11/2003 | Dunsky et al. | 219/121.75 |
| 2004/0150887 A1 * | 8/2004 | Hirai | 359/626 |
| 2005/0000641 A1 * | 1/2005 | Hartmann et al. | 156/272.8 |
| 2005/0205534 A1 * | 9/2005 | Caldwell | 219/121.63 |
| 2006/0004323 A1 * | 1/2006 | Chang et al. | 604/28 |
| 2007/0019691 A1 * | 1/2007 | Monch et al. | 372/22 |

FOREIGN PATENT DOCUMENTS

| | | | |
|---|---|---|---|
| DE | 19852266 A1 * | 5/2000 | |
| EP | 000365180 A2 * | 4/1990 | |
| FR | 1580756 A * | 9/1969 | |
| JP | 362128184 A * | 6/1987 | |
| JP | 63214707 A * | 9/1988 | |
| JP | 409295175 A * | 11/1997 | |
| JP | 11261159 A * | 9/1999 | |
| WO | WO9704915 A1 * | 2/1997 | |
| WO | WO 97/32624 | 9/1997 | |

* cited by examiner

Row 1

Row 2

FIG. 8

METHOD OF APPLYING ONE OR MORE ELECTROMAGNETIC BEAMS TO FORM A FUSION BOND ON A WORKPIECE SUCH AS A MEDICAL DEVICE

BACKGROUND OF THE INVENTION

Medical catheters having a balloon mounted thereon are useful in a variety of medical procedures. Balloon catheters may be used to widen a vessel into which the catheter is inserted by dilating the blocked vessel, such as in an angioplasty procedure. Balloon catheters may also be used to expand and/or seat a medical device such as a stent or graft at a desired position within a body lumen. In all of these applications, fluid under pressure is supplied to the balloon through an inflation lumen in the catheter, thereby expanding the balloon.

It is essential in the manufacture of balloon catheters to properly seal the balloon to the catheter. The seal must be able to withstand the high pressures to which it is subjected on inflation of the balloon. A poor seal may result in leakage of inflation fluid and inability to achieve the desired pressure or even rapid loss of pressure and deflation of the balloon.

Such seals may be formed using a fusion-based thermal bonding method such as disclosed in U.S. Pat. No. 5,501,759 to Forman involves the use of a beam of laser radiation at a wavelength selected to at least approximately match a wavelength of maximum spectral absorption of the polymeric materials forming the balloon member and body. The polymeric materials are melted by the radiation and then allowed to cool and solidify to form a fusion bond between the catheter tube and the balloon. In order to bond the balloon about its entire circumference to the catheter tube, the catheter tube may be rotated relative to the laser beam or the laser beam may be rotated relative to the catheter tube. Thus the bonds that are formed in this way are limited to bonds that are symmetric about the axis of rotation. The laser beam is typically focused onto the polymeric materials by one or more lenses or other optical arrangements.

The use of a focused laser beam in a thermal bonding process presents a number of limitations because the energy density that is applied to the polymeric materials is increased. For example, three-dimensional alignment of the beam and the catheter is critical because a focused beam has a relatively small spot size and a limited depth of focus. Alignment tolerances become even more stringent because the laser beam generally has a gaussian or near Gaussian distribution across its width. Such a distribution gives rise to an energy density that is greatest at the center of the beam and which decreases toward the beam edge. Thus, in order to maintain a uniform power level across the bond site, not only must the bond site be aligned with the focused beam, but it also must be aligned within the focused beam at the precise location at which the desired energy density is to be achieved.

In addition to more severe alignment requirements, the use of a focused beam also requires a higher degree of power stability than with the use of an unfocused beam. This is because a factor of two decrease in the diameter of the focused beam size gives rise to a factor of four increase in power density. As a result, relatively small power fluctuations that occur when the beam is generated become magnified when the beam is focused. For example, if an unfocused beam delivers 1 watt of power with a 4 mm beam diameter, the power density would be approximately 0.08 w/mm$^2$. However, if the beam is focused to a 1 mm diameter, the power density increases to about 1.3 w/mm$^2$. Thus a small percentage change in the power of the beam when it is generated can lead to large power fluctuations after the beam is focused. Delivery of a precisely controlled energy density is particularly important when the materials to be bonded are polymeric materials that have relatively low energies of transformation and which can undergo a transition from a bonding state to a burned state very easily.

Of course, for laser welding a certain average power is required to melt and bond or weld polymers. If a larger diameter beam is employed the laser power needs to be increased commensurately to obtain the same average power needed to form the bond. Thus, regardless of the beam diameter a 10% power fluctuation is still a 10% change about the optimum power and adds uncertainty to the bond conditions.

If the catheter tube is rotated, rotation speeds of 400 rpm or higher are necessary to ensure even heating of the catheter tube and balloon material. Care must be taken, however, to avoid damaging the catheter during rotation. Moreover, the catheter will have a tendency to wobble as it rotates, which may cause the bond site to move in and out of the focused beam. While this problem can be reduced by securing the catheter to a fixture at multiple locations along its length, this adds to the complexity of the fixture. Finally, the materials to be bonded must remain in intimate contact as they are rotated, thus requiring some means for preventing relative motion between them. If, for example, a heat shrink material is used to form a tight joint between the materials, the size of the heat shrink material must be reduced before the bonding process is begun. That is, the size of the heat shrink cannot be reduced by the bonding process itself, but must be performed beforehand, thus necessitating an additional preparatory step before the bonding process.

Instead of rotating the catheter the laser beam may be rotated via the use of mirrors and focusing lenses. Alignment can be difficult to achieve and maintain, however, because of vibration from moving parts. The process is slow because of the time involved in loading and unloading the catheter and for waiting for the rotational beam to reach the desired speed. Moreover, such an arrangement can be expensive to build.

SUMMARY OF THE INVENTION

In accordance with the present invention, a process and apparatus is provided for forming a fusion bond between two materials. The process begins by forming a bond site by positioning a portion of a first body with respect to a portion of a second body. At least one collimated beam of electromagnetic energy is generated and directed onto portions of the first and second bodies within the bond site so that at least one fusion zone having an increased temperature is formed.

In accordance with one aspect of the invention, the collimated beam of energy has a diameter that is greater than the bond site.

In accordance with another aspect of the invention, a power distribution along a cross-sectional portion of the collimated beam of energy impinging upon the bond site is substantially constant.

In accordance with another aspect of the invention, the collimated beam comprises first and second collimated beams of electromagnetic energy. The first and second collimated beams of energy have diameters that are at least co-linear in part and travel in opposite directions with respect to one another. The portion of the first beam is in a state of polarization orthogonal to a state of polarization of the portion of the second beam.

In accordance with another aspect of the invention, the first and second bodies remain stationary during performance of the directing step.

In accordance with another aspect of the invention, the collimated beam of energy is also a coherent beam of energy.

In accordance with another aspect of the invention, at least one of the first and second bodies is a polymeric body.

In accordance with another aspect of the invention, the first and second bodies are polymeric bodies.

In accordance with another aspect of the invention, at least one of the first and second bodies is a metal body.

In accordance with another aspect of the invention, the first and second bodies are metal bodies.

In accordance with another aspect of the invention, the first body of the forming step is a tubular polymeric catheter and the second body of the forming step is a polymeric dilatation balloon.

In accordance with another aspect of the invention, the directing step comprises directing laser energy provided by a laser beam.

In accordance with another aspect of the invention, the laser energy is generated by a $CO_2$ laser having a wavelength, for instance, of about 10.6 microns.

In accordance with another aspect of the invention, the first beam of energy is polarized and the second beam of energy is polarized so that they are in orthogonal states of polarization.

In accordance with another aspect of the invention, a cross-sectional size or shape of at least one of the first and second beams is adjusted.

In accordance with another aspect of the invention, the adjusting step is performed with an aperture traversed by beam undergoing adjustment.

In accordance with another aspect of the invention, the polymeric body is a polymeric balloon material.

In accordance with another aspect of the invention, the electromagnetic energy is substantially monochromatic.

In accordance with another aspect of the invention, the electromagnetic energy is located at a plurality of wavelengths.

In accordance with another aspect of the invention, the polymeric body is formed from a polymer selected from the group consisting of: polyesters, polyolefins, polyamides, thermoplastic polyurethanes and their copolymers, polyethylene terephthalate, nylon, and combinations thereof.

In accordance with another aspect of the invention, the energy is at least partially absorbed by the polymeric balloon material causing the polymeric balloon material to at least partially melt.

In accordance with another aspect of the invention, the polymeric body is a retention sleeve.

In accordance with another aspect of the invention, the catheter tube has a substantially circular cross-section.

In accordance with another aspect of the invention, the catheter tube has a non-circular cross-section.

In accordance with another aspect of the invention a heat shrink tubing is applied about the catheter tube at the bond site.

In accordance with another aspect of the invention, a heat shrink tubing is applied about at least one of the first and second bodies at the bond site.

In accordance with another aspect of the invention, the steps of polarizing the first and second beams are performed by first and second polarizing elements, respectively.

In accordance with another aspect of the invention, the first polarizing element transmits electromagnetic energy in a first polarization state and reflects electromagnetic energy in a second polarization state and the second polarizing element transmits electromagnetic energy in the second polarization state and reflects electromagnetic energy in the first polarization state.

In accordance with another aspect of the invention, the electromagnetic energy reflected by the first and second polarizing elements is subsequently absorbed.

In accordance with another aspect of the invention, the step of generating at least one collimated beam comprises the steps of generating an initial electromagnetic beam and splitting the initial beam into at least two beams that define the first and second beams.

In accordance with another aspect of the invention, a process is provided for forming a fusion bond between two materials. The method begins by forming a bond site by positioning a portion of a first body with respect to a portion of a second body. First and second beams of electromagnetic energy are generated, portions of which are directed onto portions of the first and second bodies within the bond site so that at least one fusion zone having an increased temperature is formed. The first and second beams of energy have diameters that are at least co-linear in part and travel in opposite directions with respect to one another. The portion of the first beam is in a state of polarization orthogonal to a state of polarization of the portion of the second beam.

In accordance with another aspect of the invention, a process is provided for forming a fusion bond between two materials. The method begins by forming a bond site by positioning a portion of a first body with respect to a portion of a second body. At least one beam of electromagnetic energy is generated. A cross-sectional size or shape of the beam is adjusted. The adjusted beam is directed onto portions of the first and second bodies within the bond site so that at least one fusion zone having an increased temperature is formed.

BRIEF DESCRIPTION OF THE DRAWINGS

FIGS. 8(*a*)-8(*f*) show the configuration of some exemplary apertures that may be employed in the present invention.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

The present invention is directed to methods and apparatuses for effectively welding or bonding workpiece components such as polymeric materials together, and in particular for bonding components of medical devices, such as catheters. Additionally an aspect of the present invention may be used to bond polymeric materials to non-polymeric materials such as metals, for example, stainless steel as well as other non-polymeric materials such as ceramics and glasses. In particular, the present invention can advantageously provide the ability to bond tubular components of polymeric materials together as are usable for making up components of medical catheters of all types.

In accordance with one aspect of the present invention, fusion welds or bonds between workpiece components such as the catheter tubing and balloon are formed by a non-contact process that uses electromagnetic radiation, resulting in bonds that are much narrower yet withstand burst pressure to the same degree as conventional bonds. Moreover, as compared to conventionally formed bonds, bonds formed according to the present invention can be positioned substantially closer to the cones of the balloon, without the crystallization or attendant stiffening. In addition, because the workpiece may remain stationary during the bonding process, the bonds that are formed need not be symmetric about the axis of rotation, thus allowing a wide variety of asymmetric as well as symmetric bonds to be formed. In addition, the bond design can be controlled to reduce the stiffness (or optimize the flexibility) of the joint while maintaining the bond strength. The invention can also be used to form a bond that is not continuous. For example, a bond may be formed that is made up of two bonding regions in close proximity to one another.

In accordance with another aspect, the present invention overcomes many of the problems and limitations of known bonding techniques that use electromagnetic radiation such as those mentioned above by directing a collimated or pseudo-collimated beam of electromagnetic energy onto the workpiece instead of a focused beam of energy. The present inventors have recognized that a number of advantages arise from the use of a collimated beam instead of focused beam. For example, because the collimation of the beam is preserved its diameter and energy density remain constant with distance. Thus, the distance between the energy source and the workpiece, as well as the alignment between the energy source and the workpiece, do not need to be controlled to a significant degree of accuracy, as required when a focused beam is employed. In addition, the bonding process is more tolerant of fluctuations in output power from the energy sources. In this way energy sources more prone to fluctuations in energy such as gas lasers may be employed.

It should be noted that strictly speaking, a collimated beam is only collimated at one point in space (i.e., at the waist of the beam) and from this point the beam is a diverging beam. If the beam waist is small the divergence is larger, if the beam waist is large the divergence is much smaller. As used herein a collimated beam includes those beams that are not only strictly collimated but those that have a relatively small divergence as well.

Preferably, the power distribution along the diameter of the coherent beam of energy impinging upon the bond site is substantially uniform. Accordingly, if the power distribution is substantially uniform across its entire diameter a bond site may be formed that has dimensions as great as the diameter of the beam. On the other hand, the power distribution of a beam is often Gaussian, i.e., the beam intensity in a plane normal to the beam is highest at the center or beam waist point and decreases as the distance from the center point increases. More specifically, for a Gaussian laser beam the beam diameter is a circle with a radius at which the intensity has dropped to $1/e^2$ or 13.5% of the peak intensity at the center of the beam. Within this circle, 95% of the laser energy is contained. In such cases the dimensions of the bond site are preferably less than the diameter of the collimated energy beam, and more preferably the bond site is sufficiently small so that it falls within that portion of the beam that does have a substantially uniform power distribution. For example, a free space laser source has a Gaussian power distribution. As discussed below, apertures may be used so that only the central portion of the Gaussian beam impinges on the workpiece. In this way the portion of the Gaussian beam impinging on the workpiece has a substantially uniform power distribution.

One example of a workpiece on which bond sites are often formed that are sufficiently small to fall within the portion of a collimated beam over which the power is uniform distributed is a catheter. Such catheters and components thereof, including balloons and other tubular components such as those defining guidewire and inflation lumens, are commonly formed from materials such as nylons, thermoplastic polyester elastomers (e.g., Hytrel®), polyethylene terephthalate (PET), polyether-block co-polyamide polymers (e.g., Pebax®), high density polyethylene, polyurethane, other polymers and copolymers, and blends thereof. Guidewire lumens are commonly provided with lubricious materials on their inner surfaces, for example, polytetrafluoroethylene or high density polyethylene, to minimize the friction between the guide wire and the surface of the catheter lumen. As such, techniques are needed to provide bonds between catheter materials and dilatation balloon materials that are consistent, fluid tight, and of sufficient strength to withstand the fluid pressures involved in balloon dilatation without sacrificing important characteristics such as pushability, trackability, crossability, and torque transmission.

Figure 1:
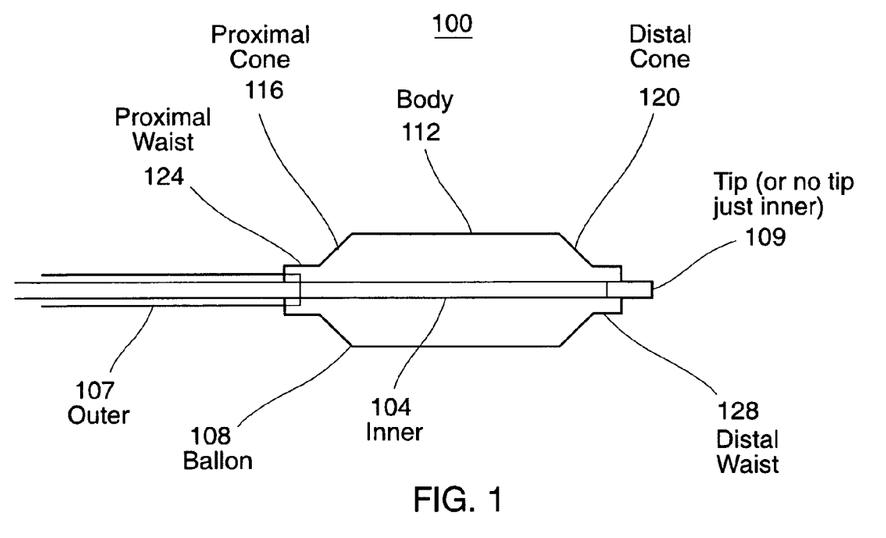
FIG. 1 shows the distal end region of a balloon catheter.

Turning to the drawings, the distal end region of a balloon catheter is shown generally at 100 in FIG. 1. The balloon catheter includes an elongated and flexible length of catheter tubing 104 constructed of a body compatible polymeric material such as a polyester. Desirably, a polyester such as Hytrel® may be used. Other suitable materials include polyolefins, polyamides and thermoplastic polyurethanes, and copolymers of these materials. A balloon 108 surrounds catheter tubing 104 along the distal end region. The balloon is shown in its fully expanded configuration, as when the balloon contains a fluid, supplied under pressure to the balloon interior through a balloon inflation lumen 107 open to the proximal end of catheter tubing 104 and to the balloon interior. In some cases catheters may also have a tip 109 located on the distal end of the catheter tubing 104.

Fully expanded, balloon 108 includes a main body region 112, disposed about catheter tubing 104, and with a diameter substantially larger than that of the tubing. The appropriate balloon and catheter tubing diameters vary, depending upon factors such as the size of the vessel or other body cavity, and the procedure involved. At opposite ends of main body region 112 are a proximal cone 116, and a distal cone 120. The proximal cone terminates in a proximal waist region 124. The inner diameter of waist region 124 is substantially equal to the outer diameter of catheter tubing 107 in the region of the proximal waist to provide an interface region along which the interior surface of waist region 124 and the exterior surface of catheter tubing 107 confront one another and are contiguous.

Distal cone 120 similarly terminates in a distal waist region 128. The distal waist also has an inner diameter substantially equal to the outer diameter of catheter tubing 104 in the region of the distal waist. Consequently, the diameter of distal waist 128 typically is less than the inner diameter of proximal waist 124 because the catheter tubing is smaller at the distal waist to allow a clearance for fluid to pass over the tubing 104 and under the balloon inflation tube 107.

Dilatation balloon 108 is desirably made from PET (polyethylene terephthalate). Other suitable materials include polyethylene, polyvinyl chloride, Surlyn® polyethylene ionomer copolymer, Pebax® polyamide-polyetherpolyester block copolymer, PBT (polybutylene terephthalate), poly(butylenes terephthalate)-block-poly (tetramethylene oxide), Arnitel, Hytrel, polyetherether ketone (PEEK), Teflon, polyetrafluoro-ethylene (PTFE), nylon (for example, nylon 12), and their copolymers as well as other polyolefins and silicone elastomers. Other suitable balloon materials are disclosed in PCT publication WO 97/32624 and commonly assigned U.S. Pat. No. 6,242,063. More generally, suitable materials include a polymeric material that is sufficiently pliable or formable to readily achieve the enlarged configuration, yet is relatively inexpansible, tending to maintain the configuration shown in FIG. 1 under increased fluid pressure within the balloon. Of course, the material should be biocompatible.

Figure 2:
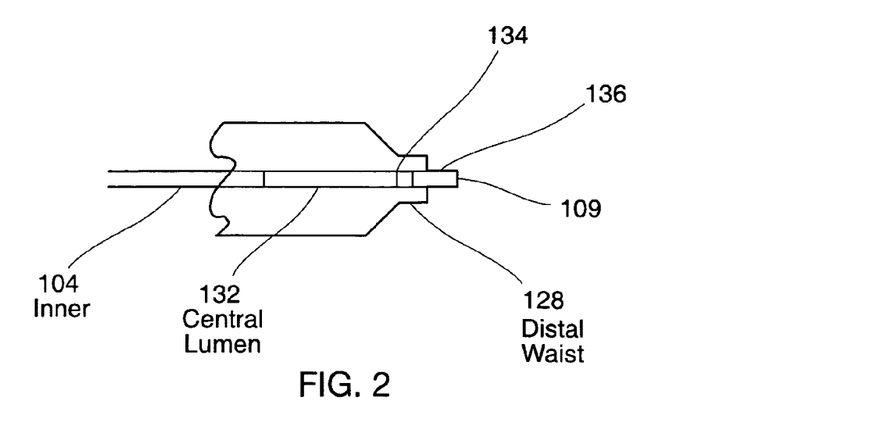
FIG. 2 shows a catheter tubing with a central lumen for accommodating a guide wire.

As shown in FIG. 2, catheter tubing 104 has a central lumen 132 to accommodate a guide wire (not shown). A line 134 indicates the proximal boundary of a fusion bond 136 between catheter tubing 104 and distal waist 128. Fusion bond 136 is annular, and is located between the distal waist 128, tip 109, and the catheter tubing 104. Typically, the polymeric material along the inside surface of distal waist 128, the inside surface of the distal tip 109 and the polymeric material along the exterior surface of tubing 104 become fused and form the bond as they cool and solidify, to provide a fluid tight seal between the catheter tubing and the balloon.

In some embodiments of the invention, bond 136 has an axial dimension of at most 0.030 inches, and is within 0.030 inches of distal cone 120, for a length of the catheter distal tip (including distal waist 128, tip, and the distal end of catheter tubing 104) of about 0.060 inches. More desirably, the axial dimension of the bond is about 0.128 inches, and the bond is within 0.020 inches of cone 120. Further, the distal cone is substantially free of undesirable crystallization that results from thermal shock from the heat of bond formation.

Figure 7:
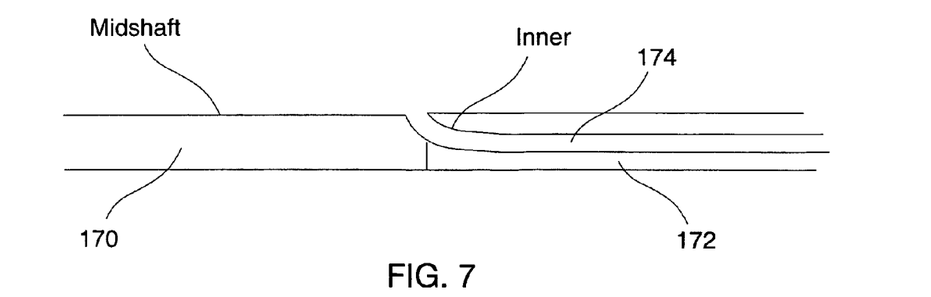
FIG. 7 shows a port bond, which is one example of an asymmetric bond that may be formed in accordance with the present invention.

As previously mentioned, since the workpiece need not be rotated during the bonding process, the present invention is particularly applicable to the formation of asymmetric bonds. For example, if the workpiece is a catheter tubing, one type of asymmetric bond that may be formed is a port bond that is provided so that a guide wire can exit the tubular wall of the catheter. FIG. 7 shows an example of a port bond in which three tubes 170, 172 and 174 are employed. Such a bond may also be formed from two tubes instead of three. Asymmetric bonds may be formed by independently controlling the power, spot size, and even the wavelength of each beam or by using differently configured apertures (discussed below) that are traversed by each beam.

Figure 3:
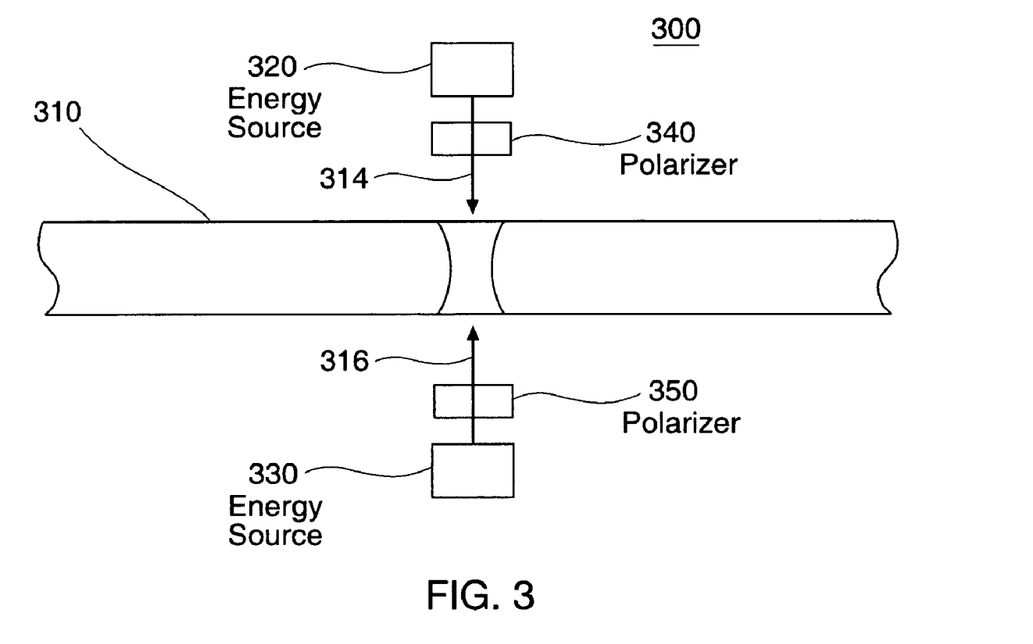
FIG. 3 is a schematic illustration of one embodiment of a welding system constructed in accordance with the present invention for welding or bonding a workpiece such as those depicted in FIGS. 1 and 2.

In FIG. 3, a schematic illustration of one embodiment of a welding system 300 for welding or bonding a workpiece 310 formed from polymeric materials in accordance with the present invention is shown. In particular, the welding system 300 that is shown and described below is particularly designed for bonding a workpiece comprising polymeric balloon catheter components and/or plural tubular polymeric catheter components together. However, the welding system 300 may additionally be utilized to bond a polymeric material to a non-polymeric material such as stainless steel.

In a welding system 300 according to the present invention, one or more electromagnetic energy sources are employed. For purposes of illustration only two electromagnetic energy sources 320 and 330 are shown in FIG. 3, which will be described in greater detail below, the purpose of which are to controllably create electromagnetic energy that is needed to weld polymeric components together. In this process, the electromagnetic energy sources 320 and 330 transmit electromagnetic energy beams 314 and 316, respectively. Energy sources 320 and 330 may be laser sources that generate coherent beams such as laser beams. For instance, the electromagnetic energy sources 320 and 330 may be $CO_2$ lasers, in which case the wavelength of the laser beams 314 and 316 is typically about 10.6 microns. $CO_2$ lasers offer a number of advantages because energy at a wavelength of 10.6 microns is relatively highly absorbed by most polymers and can be easily collimated with a relatively large beam diameter (e.g., 4.5 microns and larger). Some $CO_2$ lasers such as free space lasers generate energy beams that have a pure Gaussian distribution across its diameters, whereas other $CO_2$ lasers have energy distributions across the width of their beams that are approximately Gaussian. Finally, other $CO_2$ lasers such as waveguide lasers generate energy beams that have an approximately uniform distribution across their diameters. While $CO_2$ sources are particularly well suited for the present invention, it should be understood that any laser or other electromagnetic energy source may be used such that the functional aspects of the present invention are accomplished. For example, lasers such as diode lasers having a wavelength between about 0.8 to 1.2 microns, ND:YAG lasers having a wavelength of about 1 micron, or any other laser source that generates energy at a wavelength that is significantly absorbed by the workpiece may be employed.

As previously mentioned, in accordance with some embodiments of the present invention, the laser beam or beams (e.g., beams 314 and 316) that impinge on the workpiece 310 are collimated energy beams. If the energy source or sources are sources of coherent energy such as provided by a laser, for example, the energy beam or beams are often also collimated. If however, the source or sources do not themselves generate a collimated beam, then a separate optical element such as a collimating lens may be employed to collimate the energy generated by the laser source. Since the collimated beam or beams that impinge on the workpiece are not focused, the distance between the energy source and the workpiece, as well as the alignment between the energy source and the workpiece, do not need to be controlled to the same level of accuracy that is required when a focused beam is employed In some embodiments of the invention the catheter has a diameter that is less than the diameters of collimated energy beams 314 and 316, and preferably less than the 1/e2 portion of the beam diameters within which approximately 95% of the energy is distributed. As a result, the beams 314 and 316 may impinge on the opposing energy source. For materials with relatively slow thermal absorption rates such as plastics (as opposed to metals), a relatively wide beam can mimic a nearly flat energy profile. Since the Gaussian profile of the beam does not change with beam diameter, only kurtosis, if the diameter of the beam is too small for some applications, it can be increased without losing it Gaussian profile.

The present inventors have determined that an energy beam of an appropriate diameter impinging on a circumferential bond site of the workpiece can create a fusion bond that extends more than half way around (i.e., more than 180° C.) the circumference of the bond site. Accordingly, by directing at least two energy beams onto the circumferential bond site which originate from positions 180° C. apart from one another, as in FIG. 3, a complete circumferential bond can be created. Significantly, this can be accomplished without the need to focus the beams, thus avoiding the aforementioned problems and limitations associated with the use of a focused beam. Of course, the present invention contemplates the use of any number of energy beams. For example, three beams may be employed, in which case they may be situated 120 degrees apart from one another. Alternatively, if four beams are employed, they may be situated 90 degrees apart from one another.

As shown in FIG. 3, when two electromagnetic energy sources 320 and 330 are employed, they are preferably oriented on opposing sides of the workpiece 310 so that at least a portion of the cross-sectional diameters of collimated beams 314 and 316 are co-linear with one another. That is, if not otherwise obstructed by workpiece 310, the electromagnetic energy sources 320 and 330 are arranged so that at least a portion of collimated energy beam 316 would impinge on electromagnetic energy source 320 and at least a portion of collimated energy beam 314 would impinge on electromagnetic energy source 330.

Figure 5:
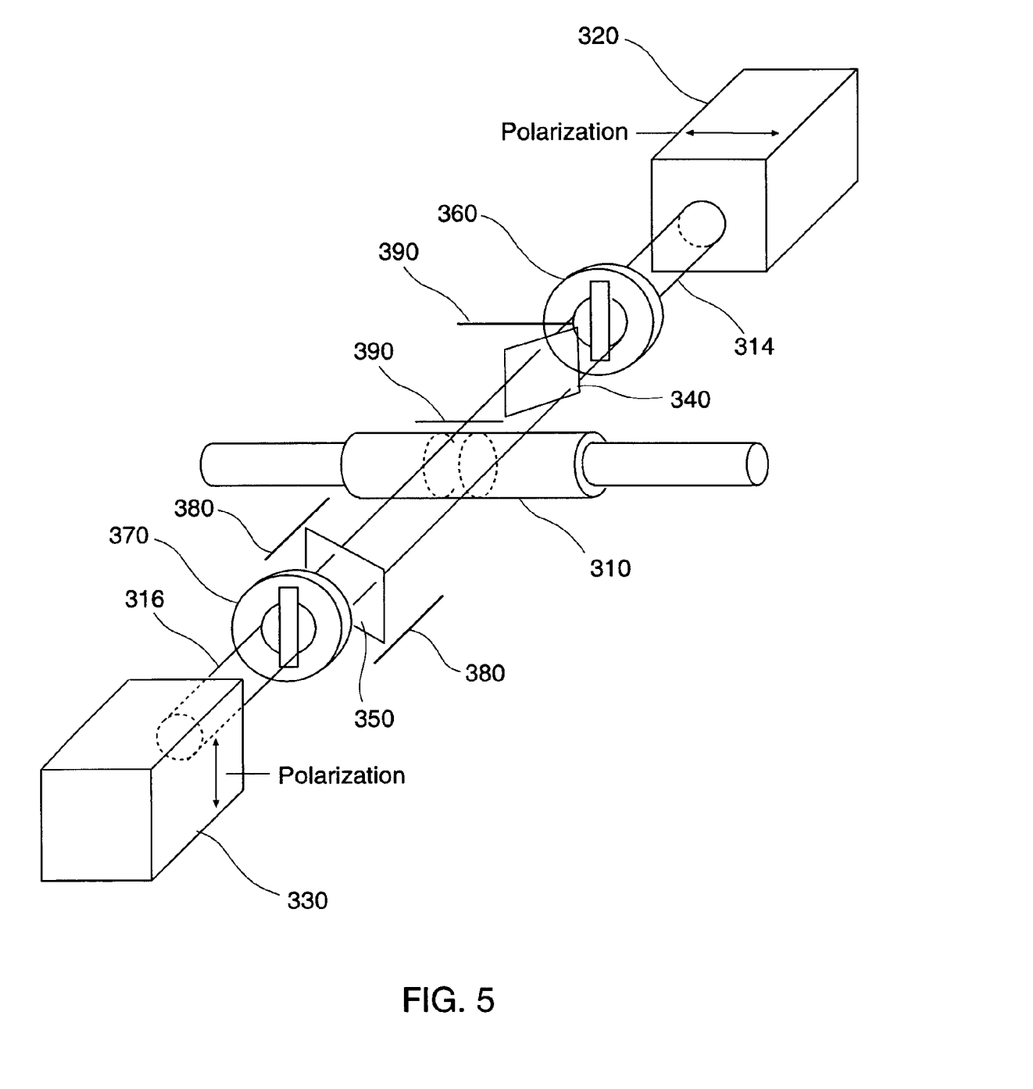
FIG. 5 is a schematic illustration of one alternative embodiment of the welding system constructed in accordance with the present invention in which each energy beam traverses a polarizing element and an aperture.

As shown in FIGS. 3 and 5, the electromagnetic energy beams 314 and 316 generated by the electromagnetic energy sources 320 and 330 respectively traverse polarizing elements 340 and 350 prior to impinging on workpiece 310. Polarizing element 340 is configured so that it only transmits energy in a single polarization state that is orthogonal to the polarization state of the energy transmitted by polarizing element 350. For example, if polarizing element 340 only transmits energy in an S-polarized state, then polarizing element 350 should only transmit energy in a P-polarized state. It should be noted that the energy orthogonally polarized with respect to the energy transmitted by the polarizing element may be either reflected or absorbed, depending on the particular polarizing element that is employed.

By using orthogonal polarizing elements 340 and 350, electromagnetic energy beam 314 will be prevented from impinging on the output face of electromagnetic energy source 330, which could otherwise adversely impact energy source 330. Likewise, electromagnetic energy beam 316 will be prevented from impinging on the output face of electromagnetic energy source 320. In this way electromagnetic energy sources 320 and 330 can be positioned on opposite sides of the workpiece 310 without interfering with one another. Thus, the use of orthogonally polarized energy beams in this manner to prevent damage to energy sources that are diametrically opposed to one another may be useful in applications in which the beams are collimated and even in applications in which the beams are focused onto the workpiece.

Energy sources 320 and 330 may generate energy in polarization states that are orthogonal to one another, or they may both generate light that is randomly polarized. If, for example, energy source 320 generates energy that is S-polarized and energy source 330 generates energy that is P-polarized, when energy from energy source 320 strikes polarizing element 340 it will pass through because polarizing element 340 is oriented to transmit S-polarized energy. However, when this S-polarized energy strikes polarizing element 350, it will reflected because polarizing element 350 is oriented to only transmit P-polarized energy. Similarly, when energy from energy source 330 strikes polarizing element 350 it will pass through because polarizing element 350 is oriented to transmit P-polarized energy. However, when this P-polarized energy strikes polarizing element 340, it will reflected because polarizing element 340 is oriented to only transmit S-polarized energy.

If, on the other hand, energy source 320 and 330 generate energy that is randomly polarized, when energy from energy source 320 strikes polarizing element 340 only the S-polarized portion of the energy will pass through. Similarly, when energy from energy source 330 strikes polarizing element 350 only the P-polarized portion of the energy will pass through. As above, once the P-polarized energy from energy source 330 strikes polarizing element 340, the energy will be reflected and the S-polarized energy from energy source 320 striking polarizing element 350 will be reflected, thereby protecting energy sources 320 and 330 from external sources of energy.

In some embodiments of the invention only a single randomly polarized energy source may be employed to achieve the same result that is achieved by using two energy sources that provide two beams with orthogonal polarizations. In this case, randomly polarized energy from the single energy source, such as source 320, for example, strikes polarizing element 314 and the S-polarized energy is transmitted therethrough. The P-polarized portion of the energy reflected by polarizing element 340 may be reflected by a suitable reflecting element or elements (not shown) so that it is incident on the workpiece from the direction diametrically opposing the S-polarized energy.

While FIG. 3 shows discrete polarization elements, those or ordinary skill in the art will recognize that the polarization elements may be integrated with the energy sources or eliminated completely if the energy sources are of a type that generate energy in only a single polarization state. The polarization elements may also be eliminated if the workpiece and source have the same diameter or if the energy sources are resilient to damage from the opposing energy beams. In addition, polarizing elements 340 and 350 may each comprise polarizing arrangements that each include more than one individual element. For example, each polarizing arrangement may include two polarizing elements that have their axes of polarization oriented at 45 degrees with respect to one another. A Faraday rotator is inserted between the two polarizing elements and rotates the polarization of the energy striking it by 45 degrees. In this way energy that traverses the first polarizing element has its polarization rotated by 45 degrees so that will pass through the second polarizing element. However, when energy from one of the polarizing arrangements strikes the other polarizing arrangement, the energy traverses the first of the polarizing elements and is reflected from the second of the polarizing elements.

FIG. 5 shows a schematic illustration of one embodiment of the welding system 300 in which the polarizing elements 340 and 350 reflect the electromagnetic energy that is in a polarization state that is orthogonal to the electromagnetic energy that is transmitted to workpiece 310. In FIGS. 3 and 5, like reference numerals refer to like elements. As shown, polarizing elements 340 and 350 are oriented so that the beams are incident upon the respective elements 340 and 350 at a suitable angle that allows the reflected component can be conveniently removed. In this way the reflected components and the transmitted components of the beam form an angle of 90° C. with respect to one another. Baffles 380 and 390 may be provided at appropriate locations around the polarizing elements 340 and 350 to absorb the reflected components of the beam. To simplify the alignment process, baffles 380 and 390, as well as the polarizing elements 340 and 350, may be secured to the energy sources 320 and 330.

Of course, in those embodiments of the invention in which the energy sources are not diametrically opposed to one another, no polarizing elements are required. For example, if three energy sources are provided that are situated 120 degrees apart from one another, the polarizing elements need not be employed, whereas if four energy sources are provided that are situated 90 degrees apart from one another, the polarizing elements may be advantageously employed.

Figure 4:
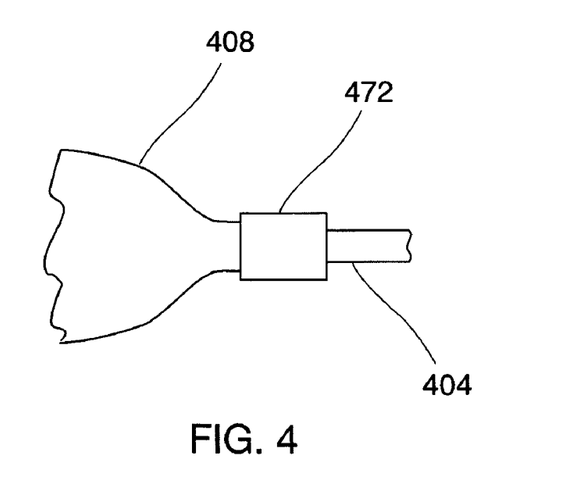
FIG. 4 shows a bond site that is enclosed by a heat shrink tubing.

In some embodiments of the invention a heat shrink material may be disposed about the bond site. The heat shrink material advantageously serves as a heat transfer element or thermal diffuser that facilitates creation of a bond with uniform characteristics. The use of a heat shrink material is particularly advantageous when, as in FIG. 3, the bond site has a circumferential configuration, in which case the heat shrink material generally has a tubular configuration. In this case the heat shrink tubing can sufficiently diffuse the heat so that the resulting bond is virtually completely uniform, despite the use of a stationary workpiece and only two electromagnetic energy sources diametrically opposed to one another. For example, if as shown in FIG. 4 the workpiece is a catheter tube 404 to be bonded to a balloon 408, heat shrink tubing 472, which is formed from a material such as polyolefin, for example, may be disposed around the tube 404 at a desired location. When heat shrink tubing is employed, the portion of the balloon to be bonded to the catheter tube, typically the proximal and/or distal waist region, is inserted within the heat shrink tubing. The balloon may also be positioned around the catheter first and the heat shrink tubing subsequently positioned over the desired portion of the balloon.

In some embodiments of the invention an aperture or mask may be placed in the beam path to provide bonds of different shapes and sizes. For example, in FIG. 5, beam 314 traverses aperture 360 and beam 316 traverses aperture 370. The apertures are employed to controllably adjust the cross-sectional shape of the beams, which in turn allows the size and shape of the resulting bonds to be controllably adjusted. For example, in some cases the apertures may simply decrease the diameter of the beam so that the size of the bond can be reduced. In other cases the apertures may be defined by a series of parallel slits. The portion of the beam traversing each slit may form a distinct bond, which provides an alternative to a single, longer bond that would otherwise be formed without the presence of the aperture. If the slits are appropriately sized with respect to the wavelength of energy that is used, the beam may undergo constructive and destructive interference with itself. The locations corresponding to constructive interference will give rise to bond sites while the locations corresponding to destructive interference will give rise to gaps between the bond sites. As those of ordinary skill in the art will recognize, these locations can be determined in accordance with the equation for Fraunhoffer diffraction from multiple slits. Roughly speaking, assuming the slit widths are significantly greater than the wavelength of energy that is employed, the distance between bond sites formed in this manner is proportional to the ratio of the distance from the slits to the workpiece to the distance between adjacent slits. For instance, if a 10.6 micron beam is employed, a ratio of about 1,000 to 1 is needed to get a 1 mm distance between bond sites. If the slits are 0.1 mm apart, the distance from the slits to the workpiece would need to be about 10 mm.

The apertures 360 and 370 may be the same or different from one another, depending on the particular bond that is to be formed. By using apertures that differ from one another, for example, a circumferentially asymmetric bond can be created. Moreover, in some cases, only one of the beams may traverse an aperture. The apertures may be used in conjunction with energy beams that are collimated or, alternatively, with energy beams that are focused onto the workpiece. While in FIG. 5 the apertures are located between the polarization elements and the workpiece, the apertures may alternatively be located between the laser sources and the polarizing elements. The apertures may be used not only in those embodiments of the invention that employ polarized beams, but they may also find use in those embodiments of the invention in which the beam or beams are not arranged in any particular state of polarization.

In addition to the aforementioned polarization elements and apertures, it is contemplated that the beams 314 and 316 may also be directed through additional optical devices such as lenses and collimators (not shown) for managing the beam in accordance with the present invention. Moreover, while each of the beams 314 and 316 have been described as being generated by different energy sources, the invention also encompasses arrangements in which a single beam generated by a single source is split into two beams, with appropriate optical elements such as mirrors and the like being used to direct each beam to the appropriate locations on the workpiece.

Figure 8:
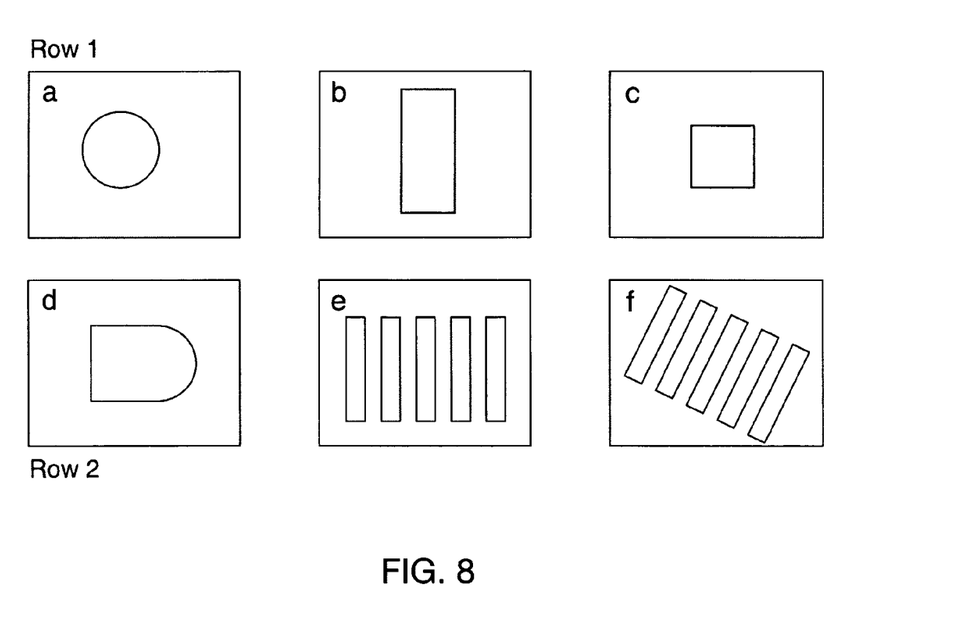

FIGS. 8(a)-8(f) show the configuration of some exemplary apertures that may be employed in the present invention. The aperture shown in FIG. 8(a) may be employed to form a spot weld, for example, whereas the aperture in FIG. 8(b) may be employed to form a narrow bond with a top hat shape in which the intensity of the laser energy perpendicular to the catheter axis is not a concern. The aperture in FIG. 8(c) is similar to that depicted in FIG. 8(b), except that the intensity of the energy in the direction perpendicular to the catheter axis is to be controlled. FIG. 8(d) shows an aperture that may be employed to form a balloon bond on the distal end. FIGS. 8(e) and 8(f) show two examples of apertures used to form multiple bonds that would increase the flexibility of the catheter yet maintain bond strength.

It is understood that the present invention may be utilized to create other fusion bond arrangements and geometries, such as lap welds, butt welds, seam welds, and the like as well as any other known or developed welding technique whereby components are located with at least portions thereof adjacent one another and thereby forming a fusion bond site in accordance with the present invention.

The concentration of energy necessary for fusion bonding at the bond site may be suitably controlled via several different parameters. First, in those embodiments of the invention in which the beam may be a focused beam, the beam may be focused over a shorter or longer length of polymeric material. Where the beam is focused over a shorter length of polymeric material, the energy source may be operated at a lower wattage or for shorter duration. Second, where the energy source is a laser, the laser beam will desirably have a profile which is constant or substantially constant across the beam diameter or a profile which is gaussian ($TEM_{00}$ mode) or substantially gaussian across the beam diameter. Third, the wavelength of the energy, desirably laser energy, and the polymeric materials of the balloon and catheter tubing will desirably be matched. That is, the polymeric materials being bonded together will desirably have a high absorptivity for energy at the selected wavelength (for example, 10.6 microns in the case of a $CO_2$ laser).

Information on the absorptivity of various materials, with respect to wavelength of the energy, is available, for example in *The Infrared Spectra* Atlas of Monomers and Polymers, published by Sadtler Research Laboratories. A more detailed discussion of the matching may be found in U.S. Pat. No. 5,501,759.

By suitably adjusting the focus of the beam and/or by providing energy at one or more wavelengths that are selected to be sufficiently absorbed by at least one and desirably both of polymeric materials, heat sufficient to fuse an outer surface of the catheter tubing and an inner surface of distal waist of the balloon may be generated at a laser power of less than 10 watts. In some cases a duration of about 0.5 seconds to about 3 seconds of laser energy application has been found satisfactory for forming bonds that can withstand burst pressures exceeding 400 pounds per square inch, and the degree of control over the laser yields a high degree of consistency among the bonds. Typically, the laser energy is applied continuously for a period of 1 to 2 seconds at a power level of 1 Watt. Desirably, the laser energy will expose an approximately 1 mm wide region on the balloon. After the fused material cools and solidifies, the heat shrink tubing, if present, is removed.

Because of the high absorptivity of one or both of the polymeric materials at the chosen wavelength(s), there is no substantial conduction of heat in either axial direction away from the bond site. Also, the heat conductivity of polymers is low and the laser is on for only a short period of time. Thus, there is no undue heating of portions of the tubing and balloon near the bond which would lead to crystallization and stiffening of the polymeric materials. As such, a distal bond can be positioned within 0.010 inches of the distal cone, for example, without any substantial crystallization or stiffening of the cone.

Figure 6:
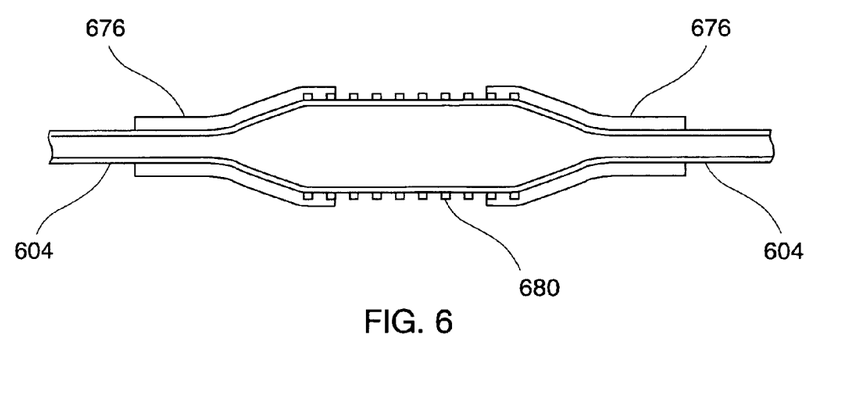
FIG. 6 shows another workpiece comprising a retention sleeve and a catheter tube.

The invention has been described above with respect to bonding a polymeric balloon material to a tubular body such as a catheter. The invention is also directed to a method of bonding a retention sleeve (such as for stents and grafts or other medical devices) or any other suitable polymeric material to a catheter tube. As shown in FIG. 6, retention sleeve 676 is fusion bonded to catheter tube 604. Retention sleeve 676 retains stent 680 on catheter tube 604. The bond is achieved using the apparatuses disclosed herein by directing the energy at the retention sleeve in the desired bond region. The retention sleeve may be made from elastic and compliant balloon materials, including materials disclosed in U.S. Pat. No. 6,068,634. Desirably, the retention sleeve will be made of a material which is radiopaque, at least in part.

As with the fusion bonding of a balloon, the retention sleeve must be suitably aligned about the desired portion of the catheter. The retention sleeve must also be suitably aligned about the stent. Optionally, as with balloons, heat shrink tubing may be disposed about the retention sleeve prior to fusion bonding. At least two beams of energy, as discussed above with respect to balloons, is then directed at the region of the desired bond to bond the retention sleeve to the catheter tube. The retention sleeve may be made of suitable polymeric materials including the balloon materials disclosed above. Other suitable materials as well as other details concerning retention sleeves may be found in U.S. Pat. No. 6,478,814 and 6,331,186.

The inventive processes may also be used to bond together two catheter tubes or a catheter tube and a sheath. An example of a catheter having a retractable sheath and a dual lumen tube is provided in U.S. Pat. No. 5,957,930. The retractable sheath disclosed therein may be bonded to the dual lumen tube using the inventive methods disclosed herein. The particular choice of energy wavelength will depend on the particular materials used for the dual lumen tube. Other portions of the catheter which may be bonded together using the inventive methods include the slide sheath and the outer shaft, the bumpers and the catheter shaft, the sliding seal and the outer shaft and the manifold and a hypotube. More generally, those polymeric portions of a catheter which are currently bonded together using other techniques may be amenable to the inventive methods.

Other uses for the inventive processes include bonding polymeric sheaths to catheter tubes, bonding sheet-like or tubular balloon protectors to balloons or catheter tubes and bonding a catheter tip to a catheter. As with the bonding of balloons to catheters, two or more beams of energy are directed at the polymeric material and catheter in the desired bonding region. The invention is also directed to bonding polymeric materials to medical balloons. For example, in the case of a catheter carrying a balloon expandable stent, a flexible sheath may be bonded to the medical balloon about the periphery of the balloon in order to protect the balloon from any edges of the stent.

The frequency of the energy which is directed at the polymeric material in the inventive processes may be chosen such that the energy is at least partially absorbed by the balloon, by the polymeric catheter tube or by both the balloon and polymeric catheter tube. The energy should be supplied at a sufficient power level as to cause at least one of and preferably both of the balloon and polymeric catheter tube to at least partially melt in the region of the desired bond.

Thus far, the energy has been described as monochromatic. The invention also contemplates the use of non-monochromatic energy as long as the energy is properly focused and of sufficient intensity to cause melting of the polymeric material to which it is directed. As such, multiple frequencies of energy may be employed as long as the energy contains one or more frequencies which are strongly absorbed by at least one of the polymeric materials. Desirably, substantially all of the frequencies of energy will be strongly absorbed by at least one of the polymer materials.

The inventive processes may also be used to bond together multiple layers of polymeric materials. For example, the inventive processes may be used to simultaneously bond a stent retention sleeve to a balloon and the balloon to a catheter. This would, of course, require proper alignment of the balloon, retention sleeve and catheter. Also desirably, the balloon, retention sleeve and catheter will all strongly absorb energy of same wavelength or will all have overlapping absorption bands.

The invention may also be used to join together tubular members that have a non-circular cross-section. Thus, for example, the inventive processes may be used to bond a balloon to a tube with an elliptical cross-section.

Selectively welding only a portion of the circumference or periphery of the catheter may prove beneficial in catheter formation, such as in the region of the port bond where a guidewire enters a catheter in its mid-section.

The invention may also be practiced by moving the catheter axially during the application of laser energy. This allows for additional control of both the amount of energy delivered to the bonding site and the flow of material. When movement of the catheter is slow, more power is delivered to the bonding site. When movement of the catheter is fast, less power is delivered to the bonding site. Moreover, in this way, a longer weld or bond may be achieved or more flow of the material may occur. This may prove particularly useful in welding a soft tip onto the end of a catheter tube where, typically, weld lengths are from about 2 mm to about 55 mm in length. When the catheter is moved perpendicular to the optical axis during welding, the beams effectively move along the catheter thereby creating a continuous bond or weld of desired length.

Varying the movement speed of the catheter may also be beneficial where the thickness of the materials to be welded varies along the length of the region to be welded. Where a thicker region is encountered, the rate of movement of the catheter may be slowed down to apply more energy thereto. Where a thinner region is encountered, the rate may be increased as less energy is needed to heat the material.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A process for forming a fusion bond between two materials comprising the steps of:
   forming a bond site by positioning a portion of a first body with respect to a portion of a second body;
   generating first and second collimated beams of electromagnetic energy; and
   directing first and second collimated beams of electromagnetic energy onto portions of the first and second bodies within the bond site so that at least one fusion zone having an increased temperature is formed, wherein said first and second collimated beams of energy have diameters that are at least co-linear in part and travel in opposite directions with respect to one another, said first beam being in a state of polarization orthogonal to a state of polarization of the second beam.

2. The process of claim 1 wherein the collimated beam of energy has a diameter that is greater than the bond site.

3. The process of claim 2 wherein a power distribution along a cross-sectional portion of the collimated beam of energy impinging upon the bond site is substantially constant.

4. The process of claim 1 wherein the first and second bodies remain stationary during performance of the directing step.

5. The process of claim 4 wherein the collimated beam of energy is also a coherent beam of energy.

6. The process of claim 1 wherein at least one of the first and second bodies is a polymeric body.

7. The process of claim 1 wherein the first and second bodies are polymeric bodies.

8. The process of claim 1 wherein at least one of the first and second bodies is a metal body.

9. The process of claim 1 wherein the first and second bodies are metal bodies.

10. The process of claim 1 wherein the first body of the forming step is a tubular polymeric catheter and the second body of the forming step is a polymeric dilatation balloon.

11. The process of claim 1 wherein the directing step comprises directing laser energy provided by a laser beam.

12. The process of claim 11 wherein the laser energy is generated by a CO2 laser, the laser energy having a wavelength of about 10.6 microns.

13. The process of claim 1 further comprising the steps of polarizing the first beam of energy and polarizing the second beam of energy so that they are in orthogonal states of polarization.

14. The process of claim 1 further comprising adjusting a cross-sectional size or shape of at least one of the first and second beams.

15. The process of claim 14 wherein the adjusting step is performed with an aperture traversed by said at least one of the first and second beams.

16. The process of claim 6 wherein the polymeric body is a polymeric balloon material.

17. The process of claim 1 wherein the electromagnetic energy is substantially monochromatic.

18. The process of claim 1 wherein the electromagnetic energy is located at a plurality of wavelengths.

19. The process of claim 6 wherein the polymeric body is formed from a polymer selected from the group consisting of: polyesters, polyolefins, polyamides, thermoplastic polyurethanes and their copolymers, polyethylene terephthalate, nylon, and combinations thereof 20. The process of claim 16 wherein the energy is at least partially absorbed by the polymeric balloon material causing the polymeric balloon material to at least partially melt.

21. The process of claim 10 wherein the energy is at least partially absorbed by the polymeric catheter tube causing the polymeric catheter tube to at least partially melt.

22. The process of claim 6 wherein the polymeric body is a retention sleeve.

23. The process of claim 10 wherein the catheter tube has a substantially circular cross-section.

24. The process of claim 10 wherein the catheter tube has a non-circular cross-section.

25. The process of claim 10 further comprising the step of applying a heat shrink tubing about the catheter tube at the bond site.

26. The process of claim 1 further comprising the step of applying a heat shrink tubing about at least one of said first and second bodies at the bond site.

27. The process of claim 13 wherein the steps of polarizing the first and second beams are performed by first and second polarizing elements, respectively.

28. The process of claim 27 wherein said first polarizing element transmits electromagnetic energy in a first polarization state and reflects electromagnetic energy in a second polarization state and said second polarizing element transmits electromagnetic energy in the second polarization state and reflects electromagnetic energy in the first polarization state.

29. The process of claim 28 further comprising the step of absorbing the electromagnetic energy reflected by the first and second polarizing elements.

30. The process of claim 1 wherein the generating step comprises the steps of generating an initial electromagnetic beam and splitting the initial beam into at least two beams that define first and second beams.

31. The process of claim 7 wherein at least one of the polymeric bodies is a polymeric tube.

32. The process of claim 7 wherein said first and second polymeric bodies are polymeric tubes.

* * * * *